United States Patent
Park et al.

(10) Patent No.: US 11,793,707 B2
(45) Date of Patent: Oct. 24, 2023

(54) VISION IMPROVING DEVICE

(71) Applicant: EDENLUX CORPORATION, Changwon-si (KR)

(72) Inventors: Sung-yong Park, Busan (KR); Kyung-hyun Nho, Busan (KR)

(73) Assignee: EDENLUX CORPORATION, Changwon-si (KR)

(*) Notice: Subject to any disclaimer, the term of this patent is extended or adjusted under 35 U.S.C. 154(b) by 959 days.

(21) Appl. No.: 16/369,255

(22) Filed: Mar. 29, 2019

(65) Prior Publication Data
US 2019/0224066 A1  Jul. 25, 2019

Related U.S. Application Data

(63) Continuation of application No. PCT/KR2017/011094, filed on Oct. 2, 2017, which is (Continued)

(51) Int. Cl.
*A61H 5/00* (2006.01)
*A61B 3/00* (2006.01)
(Continued)

(52) U.S. Cl.
CPC .......... *A61H 5/00* (2013.01); *A61B 3/00* (2013.01); *A61B 3/09* (2013.01); *G02B 7/02* (2013.01);
(Continued)

(58) Field of Classification Search
CPC ........... A61H 5/00; A61H 2201/1215; A61H 2201/165; A61H 2201/1666;
(Continued)

(56) References Cited

U.S. PATENT DOCUMENTS

| 4,408,846 A |   | 10/1983 | Balliet |
|---|---|---|---|
| 4,778,268 A | * | 10/1988 | Randle ............. A61B 3/09 351/203 |

(Continued)

FOREIGN PATENT DOCUMENTS

| CN | 101277669 A | 10/2008 |
|---|---|---|
| CN | 101843473 A | 9/2010 |

(Continued)

OTHER PUBLICATIONS

Japanese Patent Office, Office Action dated Aug. 31, 2021 in Japanese Patent Application No. 2019-516539 (13 pages).

(Continued)

*Primary Examiner* — Justine R Yu
*Assistant Examiner* — Benjamin M. Kusiak
(74) *Attorney, Agent, or Firm* — TROP, PRUNER & HU, P.C.

(57) ABSTRACT

A vision training device includes a housing having at least one eyepiece unit corresponding to an eye of a user, a display that displays a target image in front of a fixation axis of the user, a lens arranged between the eyepiece unit and the display unit, a movable unit capable of moving at least one of the display and the lens along the fixation axis, and a control unit that sets at least one training range within a movable range of the display and the lens and controls the movable unit such that at least one of the display and the lens is moved within the training range.

20 Claims, 8 Drawing Sheets

Related U.S. Application Data a continuation of application No. PCT/KR2016/014739, filed on Dec. 15, 2016, and a continuation of application No. 15/281,530, filed on Sep. 30, 2016, now Pat. No. 10,512,585.

(51) Int. Cl.
*A61B 3/09* (2006.01)
*G02B 7/02* (2021.01)

(52) U.S. Cl.
CPC .............. *A61H 2201/1215* (2013.01); *A61H 2201/165* (2013.01); *A61H 2201/1666* (2013.01); *A61H 2201/501* (2013.01); *A61H 2201/5005* (2013.01); *A61H 2201/5043* (2013.01); *A61H 2205/024* (2013.01)

(58) Field of Classification Search
CPC ...... A61H 2201/5005; A61H 2201/501; A61H 2201/5043; A61H 2205/024; A61H 5/005; A61H 2201/0107; A61H 2201/0157; A61H 2201/0176; A61H 2201/0192; A61H 2201/1207; A61H 2201/1515; A61H 2201/1604; A61H 2201/5007; A61H 2201/5028; A61H 2201/5092; A61H 2205/022; A61B 3/00; A61B 3/09; G02B 7/02; A61F 9/00; A63B 21/4003; A63B 23/025–03
USPC ......................................................... 351/203
See application file for complete search history.

(56) References Cited

U.S. PATENT DOCUMENTS

| | | | |
|---|---|---|---|
| 4,838,677 A | 6/1989 | Bronskill et al. | |
| 5,596,378 A | 1/1997 | Kelman | |
| 2006/0103808 A1* | 5/2006 | Horie | A61H 5/00 351/202 |
| 2007/0038142 A1 | 2/2007 | Todd et al. | |
| 2009/0168016 A1* | 7/2009 | Ohkawa | A61H 5/00 351/203 |
| 2009/0225275 A1* | 9/2009 | Horie | A61H 5/00 351/203 |
| 2010/0118272 A1 | 5/2010 | Iwasaki et al. | |
| 2012/0069296 A1 | 3/2012 | Li et al. | |
| 2014/0303687 A1* | 10/2014 | Wall, III | G02C 5/001 607/54 |
| 2016/0091720 A1* | 3/2016 | Stafford | G02B 27/0172 345/8 |
| 2017/0296421 A1* | 10/2017 | Travers | A61H 5/00 |
| 2017/0316264 A1* | 11/2017 | Gustafsson | G06F 3/012 |
| 2018/0032103 A1* | 2/2018 | Eskilsson | G06F 3/011 |
| 2018/0263488 A1* | 9/2018 | Pamplona | A61B 3/0041 |

FOREIGN PATENT DOCUMENTS

| | | | |
|---|---|---|---|
| CN | 104473754 A * | 4/2015 | |
| JP | S52131688 A | 11/1977 | |
| JP | H08206166 A | 8/1996 | |
| JP | H08257078 A | 10/1996 | |
| JP | H0956764 A | 3/1997 | |
| JP | H10314211 A | 12/1998 | |
| JP | 2003047636 A | 2/2003 | |
| JP | 2004298251 A | 10/2004 | |
| JP | 2004351103 A | 12/2004 | |
| JP | 2006055271 A | 3/2006 | |
| JP | 200729659 A | 2/2007 | |
| JP | 2008036086 | 2/2008 | |
| JP | 2009153658 A | 7/2009 | |
| JP | 2010088539 A | 4/2010 | |
| JP | 2010148738 A | 7/2010 | |
| JP | 2014038302 A | 2/2014 | |
| KR | 100526023 B1 | 11/2005 | |
| KR | 101370588 B1 | 3/2014 | |
| KR | 101408237 B1 | 6/2014 | |
| KR | 101580477 B1 | 12/2015 | |
| KR | 101663765 B1 | 10/2016 | |
| WO | WO2007004680 A1 | 1/2007 | |
| WO | WO2007037432 | 4/2007 | |
| WO | WO-2012035336 A1 * | 3/2012 | ............. A61B 3/032 |

OTHER PUBLICATIONS

Chinese Patent Office, Office Action dated May 18, 2021 in Chinese Patent Application No. 201780061043.2 (7 pages).

European Patent Office, Office Action dated Apr. 26, 2021 in European Patent Application No. 17856865.5 (4 pages).

Chinese Patent Office, Decision on Rejection dated Nov. 16, 2021 in Chinese Patent Application No. 201780061043.2 (14 pages).

Chinese Patent Office, Office Action dated Oct. 12, 2020 in Chinese patent application No. 201780061043, with brief translation, 11 pages total.

European Patent Office, Supplementary European Search Report dated Apr. 28, 2020 in European patent application No. 17 856 865.5, 6 pages total.

European Patent Office, Examination Report dated May 15, 2020 in European patent application No. 17 856 865.5, 1 page total.

Japanese Patent Office, Notice of Reasons for Rejection dated Apr. 12, 2022 in Japanese Patent Application No. 2019-516539 (8 pages).

India Patent Office, Office Action dated Dec. 7, 2021 in Indian Patent Application No. 201927015719 (5 pages).

Vietnam Patent Office, Office Action dated Jul. 28, 2022 in Vietnam Patent Application No. 1-2019-02119 (3 pages).

Singapore Patent Office, Notice of Eligibility for Grant and Supplementary Examination Report dated Oct. 5, 2022 in Singapore Patent Application No. 11201902806Y (4 pages).

Japanese Patent Office, Decision for Grant dated Sep. 27, 2022 in Japanese Patent Application No. 2019-516539 (8 pages).

European Patent Office, Communication under Rule 71(3) EPC dated Mar. 20, 2023 in European Patent Application No. 17856865.5 (44 pages).

United States Patent Office, Office Action dated Mar. 8, 2019 in U.S. Appl. No. 15/281,530 (13 pages).

International Searching Authority, International Search Report and Written Opinion dated Jul. 28, 2017 in International Application No. PCT/KR2016/014645 (14 pages).

International Searching Authority, International Search Report and Written Opinion dated Jul. 31, 2017 in International Application No. PCT/KR2016/014735 (17 pages).

International Searching Authority, International Search Report and Written Opinion dated Jul. 28, 2017 in International Application No. PCT/KR2016/014739 (12 pages).

International Searching Authority, International Preliminary Report on Patentability dated Apr. 2, 2019 in International Application No. PCT/KR2017/011094 (15 pages).

Japanese Patent Office, Notification Of Reasons For Refusal, dated Aug. 29, 2023 in Japanese Patent Application No. 2022-171635 (7 pages).

* cited by examiner

VISION IMPROVING DEVICE

CROSS REFERENCE TO RELATED APPLICATION

This application is a continuation application of PCT/KR2017/011094, which was filed on Oct. 2, 2017 which claims priority to PCT/KR2016/014739, which was filed on Dec. 15, 2016 and to U.S. application Ser. No. 15/281,530, which was filed on Sep. 30, 2016. The entire contents of each of which are incorporated herein in their entirety.

BACKGROUND

The present disclosure relates to a vision training device that trains muscles of the eyes on the basis of a status of personal vision of a user.

Human vision may be associated with a ciliary muscle of the eye. Thus, human vision can be improved or maintained by training of contracting or relaxing the ciliary muscle. However, since an individual human's ciliary muscle has varying abilities, vision training may be customized corresponding to each individual's vision.

However, training the ciliary muscle by simply changing a focal length of the eye of the user without considering the status of personal vision has a low training efficiency and is not easy for the user to adapt to. An improved vision training device would be desirable.

BRIEF SUMMARY

According to an aspect, a vision training device has a relatively high training efficiency for the ciliary muscle.

A vision training device may include a housing having at least one eyepiece unit corresponding to an eye of a user, a display that displays a target image in front of a fixation axis of the user, a lens arranged between the eyepiece unit and the display unit, a movable unit capable of moving at least one of the display and the lens along the fixation axis, and a control unit that sets at least one training range (TR) within a movable range of the display and the lens and controls the movable unit such that at least one of the display and the lens is moved within the training range.

The control unit may set an accommodation range corresponding to a range between a predetermined near point of accommodation position and a far point of accommodation position within the movable range, and the training range includes the accommodation range.

A user input unit may receive a user input signal from the user, and the near point of accommodation position and the far point of accommodation position may be set through an input of the user input signal.

A sensor module may check if the eye of the user transitions from an accommodated state to a non-accommodated state or transitions from the non-accommodated state to the accommodated state and generate an accommodation state change confirmation signal is further included, and the control unit sets the near point of accommodation position and the far point of accommodation position on the basis of the accommodation state change confirmation signal.

The control unit may measure a continuous or intermittent accommodation speed through the user input unit or the sensor module within the accommodation range, and the training speed in the training range of the display and the lens is determined by reflecting the measured speed.

The control unit may set a predetermined point of accommodation position and a far point of accommodation position within the accommodation range, and the training range includes at least a part of a fast accommodation range between the near point of accommodation position and the far point of accommodation position.

In an example, at least one second lens is arranged between the lens and the display along the fixation axis or between the lens and the eyepiece unit.

The movable unit may include a second movable unit that moves the second lens, and the second movable unit is any one of a piezo actuator, a VCM actuator, and an encoder actuator.

The movable unit may selectively move at least one of the lens and the second lens.

An image size of the target image may vary depending on a position of the display.

DETAILED DESCRIPTION

Various aspects of a vision training device and related methods according to the present disclosure are described. It is to be understood, however, that the following explanation is merely exemplary in describing the devices and methods of the present disclosure. Accordingly, any number of reasonable and foreseeable modifications, changes, and/or substitutions are contemplated without departing from the spirit and scope of the present disclosure.

In an exemplary vision training device, training the ciliary muscle is performed in consideration of the status of personal vision of the user, and thus the training efficiency is high, and the vision recovery effect is high as well.

Figure 1:
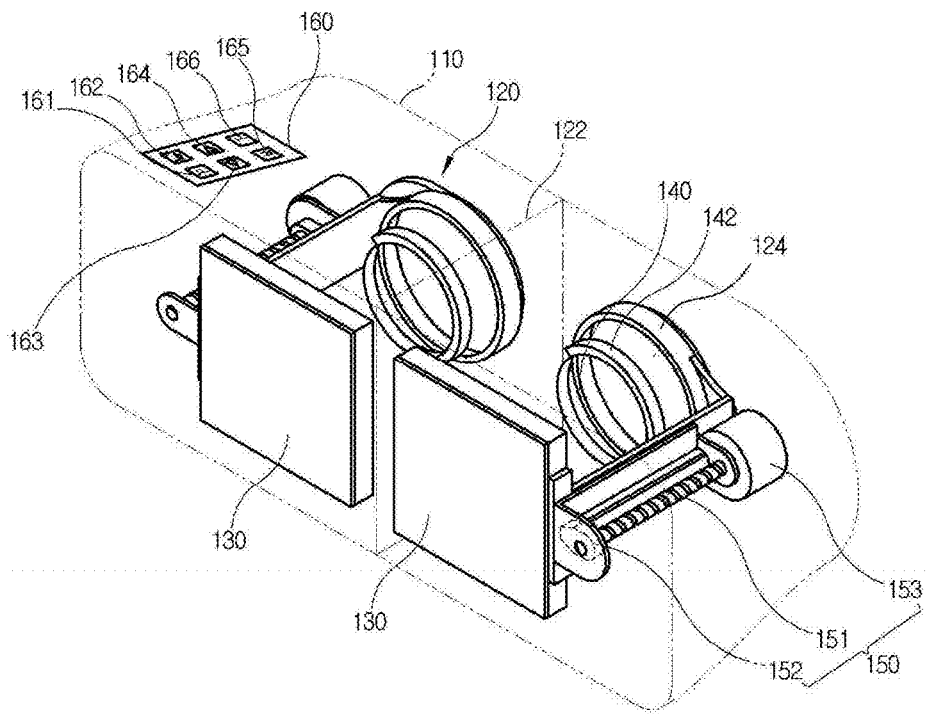
FIG. 1 is a perspective view illustrating an exemplary vision training device.

FIG. 1 is a perspective view illustrating an exemplary vision training device. As illustrated in FIG. 1, a vision training device includes a housing 110 indicated by a two-dot chain line and a pair of vision training units 120 arranged side by side in the housing 110. The housing 110 includes a shielding plate 122 which is arranged between the pair of vision training units 120 and shields the visual fields of the left and right eyes from each other. In some embodiments, the vision training units 120 may respectively have separate housing structures and the shielding plate 122 may be provided by part of the respective housings of the vision training units or omitted.

The housing 110 includes a pair of eyepiece units 124 corresponding to both eyes of the user, and the user can view the inside of the housing 110 through the eyepiece units 124. The pair of eyepiece units 124 may be connected without a shielding partition so that a through hole is formed. A user input unit 160 may receive a signal in accordance with a manipulation of the user and is installed on the upper surface of the housing 110. It will be appreciated that the user input 160 may be provided on other surfaces of the housing or as a remote unit. The user can input information or select a training condition such as a training level such as a slow accommodation range (SAR) and a fast accommodation range (FAR) to be described later, a training mode such as a training period, or the like through the user input unit 160. The housing 110 may include a strap or a device made of a material with elasticity to fix the housing 110 on the head of the user.

The vision training unit 120 includes displays 130 and lenses 140, which are respectively arranged to face each other along a fixation axis. The vision training unit 120 includes lens holders 142 that hold the lenses 140. Each of the lens holders 142 is arranged corresponding to the corresponding eyepiece unit 124. The user can see the displays 130 through the lenses 140 supported by the lens holders 142.

The display 130 displays a target image for vision training. The display 130 may be an electronic display device such as an LCD or an LED or a static display item such as paper, a plastic plate, or the like. The target image can be a static image such as a landscape, a graphic, a point, or a geometric shape or a moving picture.

The lens 140 is mounted on the lens holder 142 and arranged between the eyepiece unit 124 and the display 130. The user can view the target image displayed on the display 130 through the eyepiece unit 124 and the lens 140. The lens 140 is preferably a convex lens. The convex lens can extend the perspective of an image by changing the focal length between the eye of the user and the target image so that the user recognizes the image as if the image were at a distance farther than an actual distance. The lens 140 is not limited to a convex lens, and various types of lenses such as a polarizing lens, a color lens, and the like can be employed. In a case in which a polarizing lens or a color lens is employed, the user can view the target image which is partially filtered, e.g., partially recognized.

The display 130 and the lens holder 142 are connected by a movable unit 150. The movable unit 150 includes a lead screw 151, a movable body 152, and a drive motor unit 153. The movable body 152 may be coupled to the display 130, and the drive motor unit 153 may be coupled to the lens holder 142, or vice versa. The lead screw 151 connects the drive motor 153 with the movable body 152.

As the drive motor 153 is driven, the lead screw 151 rotates, and the display 130 and the lens 140 is moved toward or away from each other along the fixation axis. In a case in which the display 130 is fixed to the housing 110, the lens 140 is moved relative to the display 130 as the drive motor 153 is driven. In a case in which the lens holder 142 is fixed to the housing 110, the display 130 is moved relative to the lens 140 as the drive motor 153 is driven. The display 130 and the lens holder 142 may be configured to move relative to the housing 110 so that the display 130 and the lens 140 can be moved independently at the same time. A manual driving method in which the display 130 and the lens 140 are moved by a manipulation of the user may also be employed.

Figure 2:
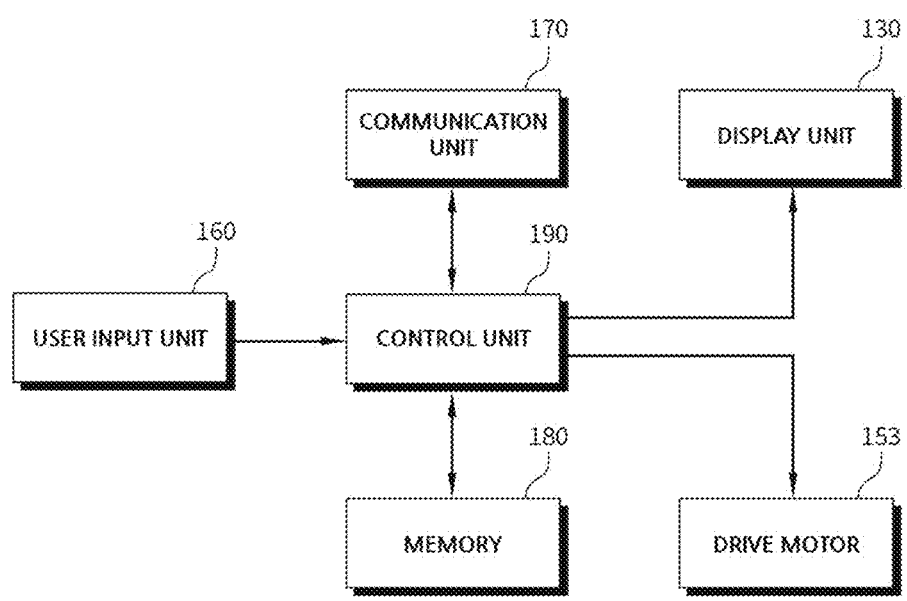
FIG. 2 is a control block diagram of an exemplary vision training device.
Figure 3A:
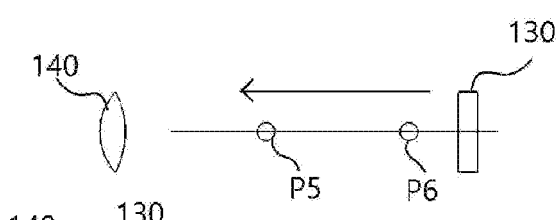
FIGS. 3A, 3B, 3C, 3D are diagrams illustrating various exemplary methods of measuring a near point of accommodation position and a far point of accommodation position in a vision training device.
Figure 3B:
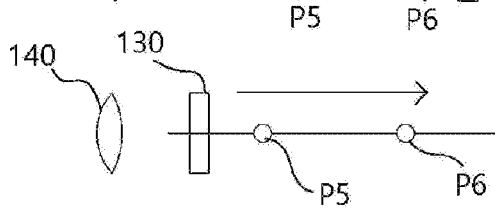
Figure 3C:
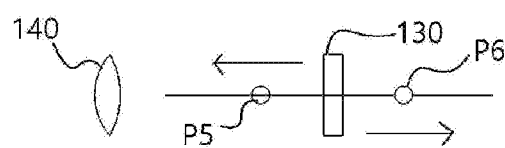
Figure 3D:
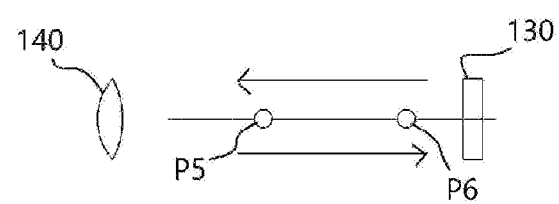

FIG. 2 is a control block diagram for an exemplary vision training device. Referring to FIGS. 1 and 2, the vision training device includes a control unit 190, which may include a processor to execute the functions described herein, that receives information input from the user input unit 160, which includes a plurality of user input buttons 161 to 166. The user input unit 160 may include a power button, a user selection button, a forward moving button, a backward moving button, a measurement mode button, and a training mode button. The user input unit 160 may be provided by a wired or wireless remote controller or may receive information using voice recognition, a gyro sensor, or an eye tracking technique using an image recognition sensor.

The vision training device may include a communication unit 170 that provides wired or wireless communication with an external device such as a smart phone, a tablet, a PC, or a user server. The communication unit 170 can perform transmission and reception of data generated in the vision training device with the external device.

The vision training device may include a memory 180 that stores user information, diopter conversion data, vision data, training data, and various types of data necessary for the operation of the vision training device. The diopter conversion data includes data obtained by converting a position of the display 130 and the lens 140 into a diopter value within a movable range of the display 130 or the lens 140.

The control unit 190 can control at least one of the pair of displays 130 and the pair of lenses 140 individually. Accordingly, in the exemplary vision training device, it is possible to freely select and train either of the left eye and the right eye or both the left eye and the right eye.

Figure 4:
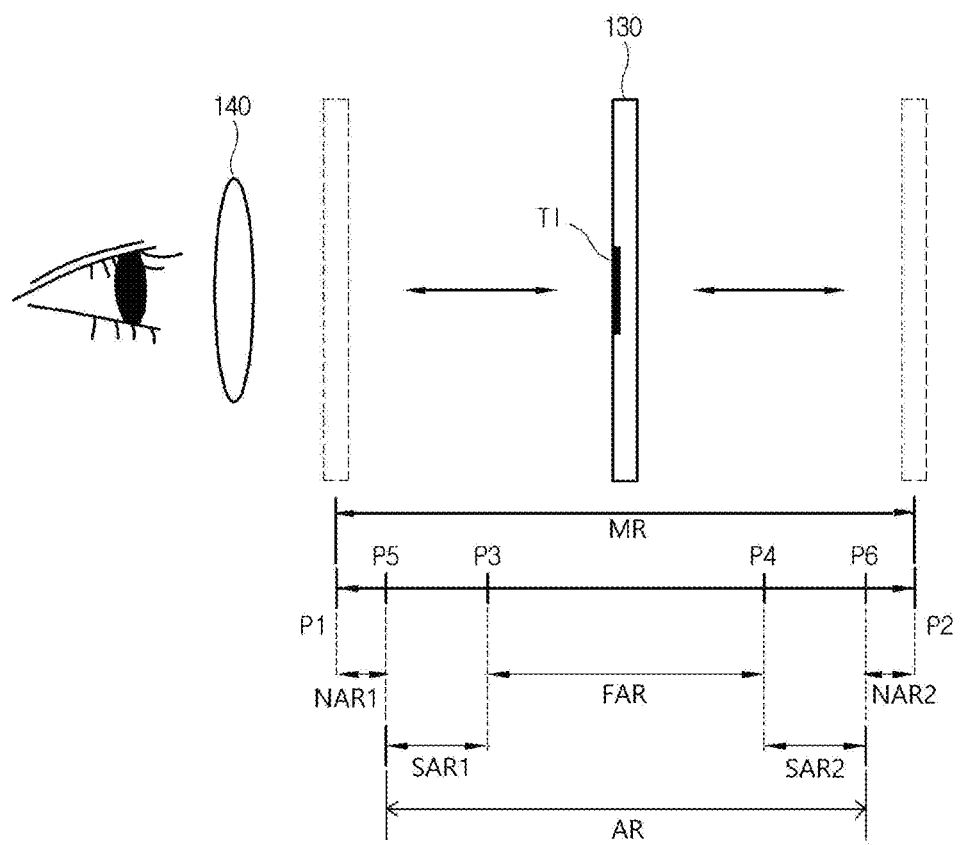
FIG. 4 is a diagram describing exemplary measurement and training processes based on display movement.
Figure 5:
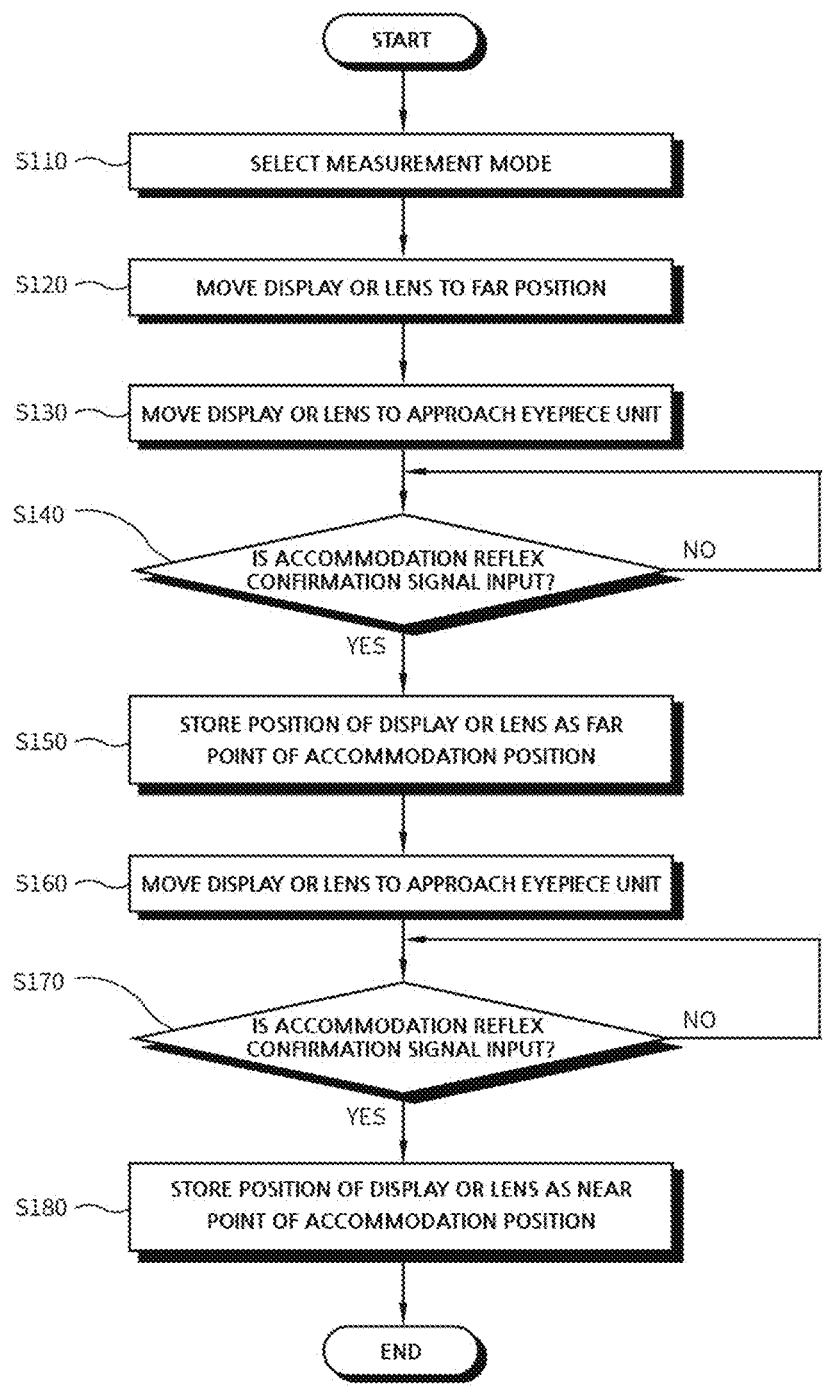
FIG. 5 is a flowchart illustrating an exemplary process of measuring a near point of accommodation position and a far point of accommodation position using a measurement method such as illustrated in (A) of FIG. 3.

FIG. 3 is an explanatory diagram illustrating various methods of measuring a near point of accommodation position P5 and a far point of accommodation position P6 in the exemplary vision training device. FIG. 4 is a reference diagram for describing measurement and training processes based on display movement. FIG. 5 is a flowchart illustrating a process of measuring or setting the near point of accommodation position P5 and the far point of accommodation position P6 using a measurement method illustrated in (A) of FIG. 3. Referring to FIGS. 3, 4, and 5, the near point of accommodation position P5 and the far point of accommodation position P6 can be measured or set while the display 130 or the lens 140 is being moved from a far position P2 to a near position P1 as illustrated in (A) of FIG. 3.

An exemplary process of operating the vision training device will now be discussed. The user may press the power button of the user input unit 160 so that the device is powered on. The user wears the vision training device and selects a measurement mode by pressing the measurement mode selection button of the user input unit 160 (S110).

When the measurement mode is selected by the user, the control unit 190 controls the drive motor 153 such that the display 130 or the lens 140 is moved to the far position P2 (S120). The far position P2 is the farthest position from the eyepiece unit 124 in a movable range MR of the display 130 or the lens 140 and can be adjusted within a predetermined range.

The control unit 190 controls the drive motor 153 such that the display 130 or the lens 140 is continuously or intermittently moved from the far position P2 toward the eyepiece unit 124 (step S130). The moving speed in the case of continuous moving or the intermittent moving interval in the case of the intermittent moving can be adjusted to a set speed or a set interval.

The control unit 190 checks whether or not an accommodation reflex confirmation signal is input from the user input unit 160 (S140). The accommodation reflex confirmation signal is a signal which is generated and transmitted to the control unit 190 in accordance with a manipulation of the user on the user input unit 160 when the eye of the user transitions from a non-accommodated state to an accommodated state. When a target image TI which is blurred transitions to be seen clearly as the display 130 or the lens 140 is moved, that is, at a point at which the visibility of the target image TI by the user changes, the user presses the user selection button of the user input unit 160, so that the accommodation reflex confirmation signal is input.

When the accommodation reflex confirmation signal is input from the user input unit 160, the control unit 190 stores a position of the display 130 or the lens 140 as the far point of accommodation position P6 (S150).

The control unit 190 controls the drive motor 153 such that the display 130 or the lens 140 is moved toward the eyepiece unit 124 continuously or intermittently (S160). A moving speed in the case of the continuous moving or a waiting time in a non-moving state in the case of the intermittent moving can be adjusted.

The control unit 190 checks whether or not a non-accommodation state confirmation signal is input from the user input unit 160 (S170). The non-accommodation state confirmation signal is a signal which is generated and transmitted to the control unit 190 in accordance with a manipulation of the user on the user input unit 160 when the eye of the user transitions from the accommodated state to the non-accommodated state. When the target image TI which is clear transitions to be seen blurred as the display 130 or the lens 140 is moved, that is, at a point at which the visibility of the target image TI by the user changes, the user presses the user selection button of the user input unit 160, so that the non-accommodation state confirmation signal is input.

When the non-accommodation state confirmation signal is input from the user input unit 160, the control unit 190 stores a position of the display 130 or the lens 140 as the near point of accommodation position P5 (S180). The far point of accommodation position P6 and the near point of accommodation position P5 are individually measurable.

It will be appreciated that the far point of accommodation position P6 and the near point of accommodation position P5 can be measured by other methods and the method of moving from the far position (P2) to the near position (P1) is exemplary in nature.

The near point of accommodation position P5 and the far point of accommodation position P6 can be measured while the display 130 or the lens 140 is being moved from the near position (P1) to the far position (P2) as illustrated in (B) of FIG. 3.

The control unit 190 controls the drive motor 153 such that the display 130 or the lens 140 is moved to the near position P1. Preferably, the near position P1 is a position which is closest to the eyepiece unit 124 in the movable range of the display 130 or a position which is apart from the eyepiece unit 124 by a predetermined distance.

After the display 130 or the lens 140 is moved to the near position P1, the control unit 190 controls the drive motor 153 such that the display 130 or the lens 140 is continuously or intermittently moved in a direction from the eyepiece unit 124 toward the far point P2. The moving speed in the case of the continuous moving or the waiting time in the non-moving state in the case of the intermittent moving can be adjusted.

The control unit 190 checks whether or not the accommodation reflex confirmation signal is input from the user input unit 160. When the target image TI which is blurred transitions to be seen clearly as the display 130 or the lens 140 is moved, that is, at a point at which the visibility of the target image TI by the user changes, the user presses the user selection button of the user input unit 160, so that the accommodation reflex confirmation signal is input. The control unit 190 stores the position of the display 130 or the lens 140 as the near point of accommodation position P5 at a time point at which the accommodation reflex confirmation signal is input from the user input unit 160.

The control unit 190 controls the drive motor 153 such that the display 130 or the lens 140 is continuously or intermittently moved toward the far position P2. The moving speed in the case of the continuous moving or the waiting time in the case of the intermittent moving can be adjusted.

The control unit 190 checks whether or not the non-accommodation state confirmation signal is input from the user input unit 160. When the target image TI which is clear transitions to be seen blurred as the display 130 or the lens 140 is moved, that is, at a point at which the visibility of the target image TI by the user changes, the user presses the user selection button of the user input unit 160, so that the non-accommodation state confirmation signal is input. When the non-accommodation state confirmation signal is input from the user input unit 160, the control unit 190 stores the position of the display 130 or the lens 140 as the far point of accommodation position P6. The near point of accommodation P5 and the far point of accommodation P6 need not be continuously measured, and any one of the near point of accommodation P5 and the far point of accommodation P6 may be measured.

The near point of accommodation position P5 and the far point of accommodation position P6 may be measured while the display 130 or the lens 140 is being moved with reference to a user reference position.

A middle point of a statistically average accommodation range at the user's age may be set as the user reference position, or a position at which the user can see most comfortably when the display 130 or the lens 140 is moved forward or backward at a predetermined speed within the line of sight range may be set as the user reference position in accordance with the input from the user. The near point of accommodation position P5 may be set on the basis of the signal input from the user input unit 160 when the transition from the accommodated state to the non-accommodated states is performed while the display 130 or the lens 140 is being moved toward the eyepiece unit 124. The far point of accommodation position P6 may be set while the display 130 or the lens 140 is being moved in the opposite direction.

As illustrated in (D) of FIG. 3, the near point of accommodation position P5 may be decided while the display 130 or the lens 140 is being moved from the far position P2 to the near position P1, and then the far point of accommodation position P6 may be decided while the display 130 or the lens 140 is being moved from the near position P1 to the far position P2.

In a case in which the display 130 or the lens 140 is moved from the far position P2 to the near position P1, the transition from the non-accommodated state to the accommodated state and the transition from the accommodated state to the non-accommodated state are performed. In the measurement method illustrated in (D) of FIG. 3, when the transition from the accommodated state to the non-accommodated state is performed, the near point of accommodation position P5 is decided on the basis of the signal input from the user input unit.

When the display 130 or the lens 140 is moved from the near position P1 to the far position P2, the transition from the non-accommodated state to the accommodated state and the transition from the accommodated state to the non-accommodated state are performed. In the measurement method illustrated in (D) of FIG. 3, when the transition from the accommodated state to the non-accommodated state is performed, the far point of accommodation position P6 is decided on the basis of the signal input from the user input unit. At this time, preferably, the near point of accommodation position P5 and the far point of accommodation position P6 are repeatedly measured while reducing the moving speed of the display 130 or the lens 140, and converged positions are selected as the near point of accommodation position P5 and the far point of accommodation position P6.

The near point of accommodation position P5 and the far point of accommodation position P6 can be decided by various methods other than the above-described methods. For example, the near point of accommodation position P5 and the far point of accommodation position P6 may be measured while the display 130 or the lens 140 is being moved continuously from the far position P2 to the near position P1 or from the near position P1 to the far position P2. When the moving speed of the display 130 or the lens 140 is different, positions measured as the near point of accommodation position P5 and the far point of accommodation position P6 may be different. As the moving speed of the display 130 or the lens 140 increases, the width between the near point of accommodation position P5 and the far point of accommodation position P6, which are measured, may decrease, whereas as the moving speed of the display 130 or the lens 140 decreases, the width between the near point of accommodation position P5 and the far point of accommodation position P6, which are measured, may increase.

In some examples, one of a plurality of near point of accommodation positions P5 and one of a plurality of far point of accommodation positions P6 measured by various methods as described above may be selected. For example, the position measured by the method described in (B) of FIG. 3 may be selected as the near point of accommodation position P5, and the position measured by the method described in (A) of FIG. 3 may be selected as the far point of accommodation position P6.

The near point of accommodation positions P5 and the far point of accommodation positions P6 measured in the methods illustrated in (A) to (D) of FIG. 3 may be slightly different in position. The near point of accommodation position P5 measured by the method illustrated in (B) of FIG. 3 may be desirable as the near point of accommodation position P5, and the far point of accommodation position P6 measured by the method illustrated in (A) of FIG. 3 may be desirable as the far point of accommodation position P6, but the near point of accommodation position P5 and the far point of accommodation position P6 measured by the methods illustrated in (C) and (D) of FIG. 3 may be selected.

To determine the near point of accommodation position P5 and the far point of accommodation position P6 which are reliable, it is desirable for the user to perform the above-described measurement procedure repeatedly and decide an average near point of accommodation position P5 and an average far point of accommodation position P6 as the near point of accommodation position P5 and the far point of accommodation position P6.

The vision training device according to an embodiment may extract accommodation information specific to each user on the basis of information derived by various methods of measuring the near point of accommodation position P5 and the far point of accommodation position P6. The accommodation information may be extracted on the basis of the near point of accommodation position P5 and the far point of accommodation position P6. The accommodation information may be indicated by values indicating the near point of accommodation position P5 and the far point of accommodation position P6 themselves, may be indicated by a distance value of the display 130 or the lens 140 from a reference position, or may be indicated by a diopter conversion value of a corresponding position. The near point of accommodation position and the far point of accommodation position information can be used as a parameter that is important for evaluating the vision of the user. For example, the near point of accommodation position can be used as an index indicating how close a person can see clearly, that is, an index of presbyopia, and the far point of accommodation position information can be used as an index indicating how far a person can see clearly, that is, an index of distance visual acuity. The status of the personal vision of the user is detected with this measurement mode as described above, and vision training in which the detected status of personal vision is considered is provided, so that the vision improvement effect can be increased or maximized.

The vision training device according to an embodiment may include a sensor module that detects whether the eye of the user is in the accommodated state or the non-accommodated state by emitting infrared rays or light toward the eye of the user and receiving infrared rays or light reflected from the eye of the user. The sensor module may repeatedly check if there is a change in an accommodation state of the eye of the user at set intervals. The sensor module may check if the eye of the user transitions from the accommodated state to the non-accommodated state, and transmit an accommodation state change confirmation signal to the control unit 190 when it is determined that the eye of the user transitions from the accommodated state to the non-accommodated state. The sensor module may check if the eye of the user transitions from the non-accommodated state to the accommodated state, and transmit the accommodation state change confirmation signal to the control unit 190 when it is determined that the eye of the user transitions from the non-accommodated state to the accommodated state. The control unit 190 can set the near point of accommodation position P5 and the far point of accommodation position P6 on the basis of the accommodation state change confirmation signals.

The sensor module may employ a principle similar to an examination principle of an auto refractor. The sensor module may include a light output unit that outputs infrared light or light toward the eye of the user, a light detecting unit that detects reflected light reflected from the eye of the user, and a refraction evaluating unit that calculates the focal length of the detected reflected light and calculates a position at which infrared ray or light output toward the eye focus on the eye using the focal length.

The control unit 190 sets an accommodation range AR on the basis of the near point of accommodation P5 and the far point of accommodation P6 decided in the measurement mode. The accommodation range AR corresponds to a range between the near point of accommodation position P5 and the far point of accommodation position P6. Ranges (first non-accommodation range (NAR1) and second non-accommodation range (NAR2)) outside the accommodation range AR within the movable range MR of the display 130 or the lens 140 are non-accommodation range.

Figure 6:
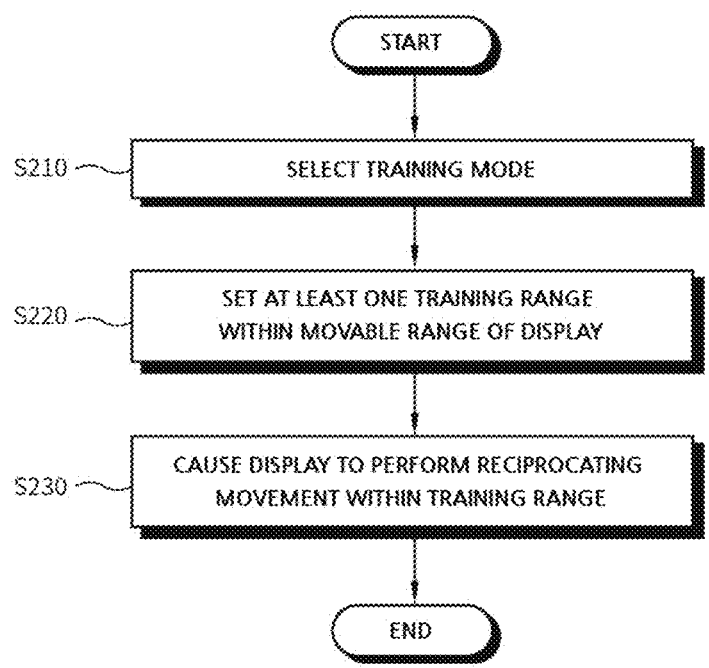
FIG. 6 is a flowchart illustrating an exemplary training mode process in a vision training device.

FIG. 6 is a flowchart illustrating an exemplary training mode process for a vision training device. The user presses the power button of the user input unit 160 so that the vision training device is powered, wears the vision training device, and selects a training mode by pressing the training mode selection button of the user input unit 160 (S210).

If the training mode is selected by the user, the control unit 190 sets at least one training range within the movable range MR of the display 130 (S220). The training range includes the accommodation range AR for effective vision improvement. The control unit 190 may set a range including the accommodation range AR and at least a part of the non-accommodation range (NAR1 and NAR2) within the movable range (MR) as the training range.

In step S230, the display 130 or the lens 140 is continuously moved in the set training range or is intermittently moved such that moving with a predetermined distance and waiting with a predetermined waiting time are repeated (step S230). When the speed at which the display 130 or the lens 140 is moved and the waiting time after the movement are set in consideration of the status of personal vision of the individual user, the vision improvement by the vision training can be more effectively achieved.

Figure 7:
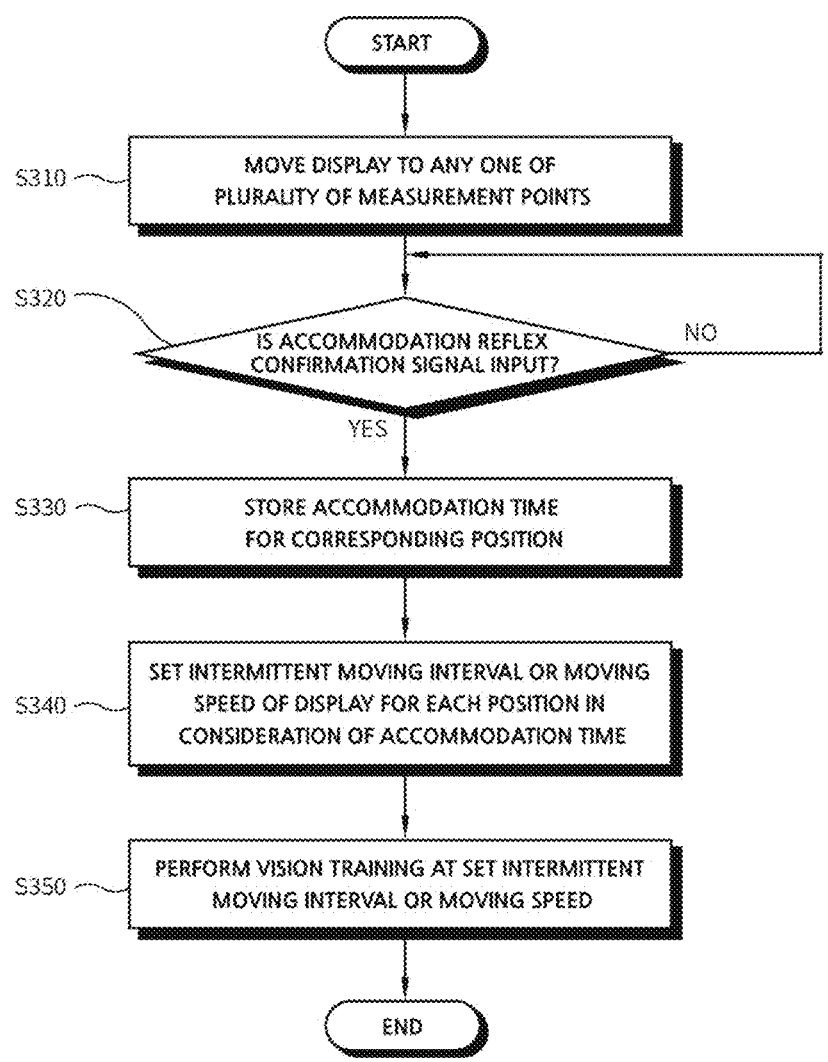
FIG. 7 is a sequence diagram illustrating an exemplary training mode process in a vision training device.
Figure 8:
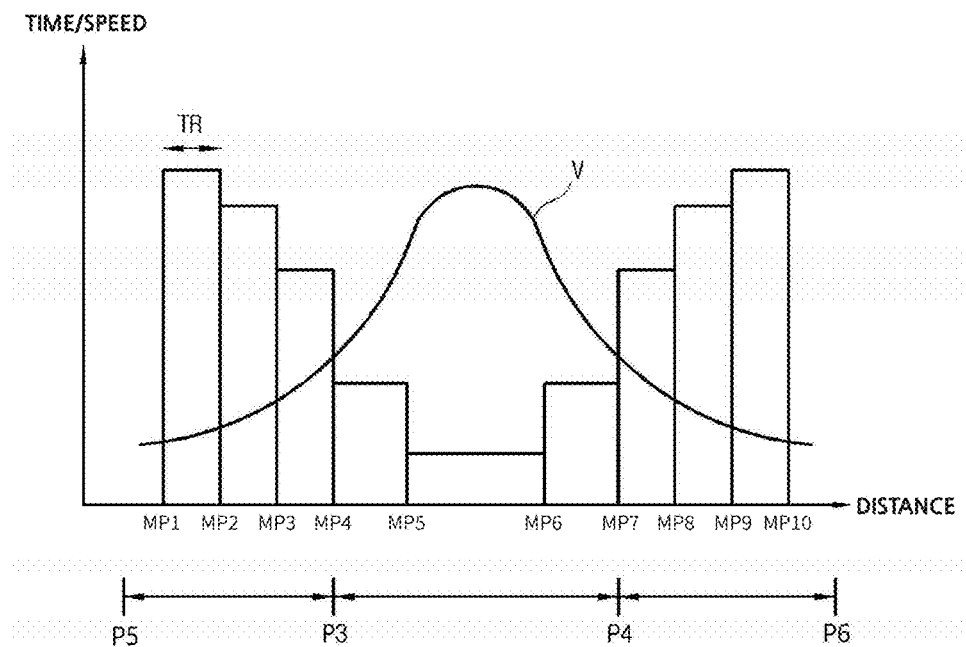
FIG. 8 is a diagram illustrating a training method according to an example illustrated in FIG. 7.

FIG. 7 is a flowchart illustrating an exemplary training mode process for a vision training device, and FIG. 8 is a reference diagram for describing a training method according to an example of FIG. 7. Referring to FIGS. 7 and 8, to set the continuous moving speed or the intermittent waiting time in which the status of personal vision of the user is reflected, in step S310, the control unit 190 controls the display 130 or the lens 140 such that the display 130 or the lens 140 is positioned at one of a plurality of measurement positions in the training range. For convenience of description, it is assumed that the display 130 or the lens 140 is moved from a first measurement position MP1 to a second measurement position MP2, but this is not limiting.

In step S320, the control unit 190 checks whether or not the accommodation reflex confirmation signal is input from the user input unit 160 or the sensor module 200. The accommodation reflex confirmation signal is a signal indicating that the target image recognized by the user becomes clear or that the eye of the user transitions to the accommodated state.

If the user presses the user input unit 160 at the point at which the target image becomes clear at the second measurement position MP2, the accommodation reflex confirmation signal is input. In a case in which the sensor module 200 is used, the sensor module 200 may repeatedly check the accommodation state of the eye of the user, and provides the accommodation reflex confirmation signal to the control unit 190 when the eye of the user transitions to the accommodated state.

When the accommodation reflex confirmation signal is input, the control unit 190 stores an accommodation time for the measurement position MP2 (S330). The accommodation time may include a period of time until the accommodation reflex confirmation signal is input after the display 130 or the lens 140 starts to be moved toward the second measurement position MP2. The accommodation time has a value that differs depending on the status of personal vision of the user. The position of the display 130 or the lens 140 in the vision training device may be converted into a predetermined diopter value, and the converted diopter value may be provided to the user.

The accommodation time can be measured for each of a plurality of measurement positions MP1 to MP10. It is desirable to measure the accommodation time for each measurement position in accordance with the moving direction of the display 130 or the lens 140. This is because, although the measurement position is the same, the accommodation time may be different depending on the position of the display 130 or the lens 140 before the target image is recognized. For example, when the display 130 or the lens 140 enters the accommodation range AR from the non-accommodation range NAR, the accommodation time at P5 is different from that when the display 130 or the lens 140 enters the non-accommodation range NAR from the accommodation range AR.

When the accommodation time is decided for each of the plurality of measurement positions, the control unit 190 sets an intermittent moving interval or the continuous moving speed V of the display 130 or the lens 140 by reflecting the decided accommodation time (S340). The intermittent moving interval includes an interval at which the display 130 or the lens 140 moves and stops at corresponding positions, and the continuous moving speed V includes a moving speed of the display 130 or the lens 140 passing a corresponding measurement position.

After the intermittent moving interval or the continuous moving speed V is set, the control unit 190 performs control such that the display 130 or the lens 140 stays or passes through a corresponding position at the set intermittent moving interval or the set moving speed at (S350).

The vision training is performed in consideration of the accommodation time for each measurement position, and thus the customized vision training in which the accommodation time of the user for the corresponding position is considered can be provided to the user. Therefore, it is possible to perform the vision training efficiently and to strengthen the ciliary muscle more effectively through the vision training.

In a range (for example, FAR) in which the accommodation time is short, a time taken for the eye of the user to accommodate to the target image TI is short, and the accommodation power of the eye of the user is high. Therefore, the width of the training range is set to be relatively large when the accommodation time is short, and the width of the training range is set to be relatively small when the accommodation time is long, and thus effective training can be performed without incurring an excessive load on the user in the training process.

When the width of the training range and the continuous moving speed and the intermittent moving interval of the display 130 or the lens 140 within the training range are variably set in consideration of the accommodation time of the user as described above, the vision improvement effect the can be increased or maximized.

In an example, to set an effective training range on the basis of the above-described information, the control unit 190 may set a near point of accommodation position P3 and a far point of accommodation position P4 within the accommodation range AR. The control unit 190 may set the near point of accommodation position P3 and the far point of accommodation position P4 in consideration of both the width of the accommodation range AR and a value related to the age of the user. For example, if the width of the accommodation range AR is large, a wide fast accommodation range FAR can be set, and as the age increases, the width of the fast accommodation range FAR can be set to decrease. A range between the nearest point of accommodation position P3 and the far adjustment reaction position P4 can be set as the fast accommodation range FAR, and ranges other than the fast accommodation range FAR within the accommodation range AR can be set as slow accommodation ranges SAR1 and SAR2. The fast accommodation range FAR can also be set by selecting two measurement points among the measurement points MP1 to MP10. The fast accommodation range FAR includes a range in which the eye of the user can perform the accommodation training comfortably and can be applied to a virtual reality (VR) technique. In this case, the eye fatigue caused by a video reproduced in a VR game or the like is reduced during the vision training, so that the user can enjoy a VR game or the like while feeling as if the training were not performed.

In an example, the control unit 190 causes the display 130 or the lens 140 to be positioned at either the near point of accommodation position P5 or the far point of accommodation position P6. Hereinafter, for the convenience of description, it is assumed that the display 130 or the lens 140 is moved to be positioned at the near point of accommodation position P5, but that is not limiting.

The control unit 190 controls the movable unit 150 such that the measurement operation in which the display 130 or the lens 140 positioned at the near point of accommodation position P5 is moved in the direction of the far position P2 by a predetermined distance and then stays at the position for a preset waiting time is repeated. A slow accommodation reflex confirmation signal is generated and input to the control unit 190, for example, when the target image (TI) recognized through the lens 140 does not become clear within a set waiting time (for example, 0.5 seconds), and so the user does not input the accommodation reflex confirmation signal through the user input unit 160. Alternatively, the slow accommodation reflex confirmation signal is generated and input to the control unit 190, for example, when the target image (TI) recognized through the lens 140 does not become clear within a set waiting time (for example, 0.5 seconds), and so the user inputs the slow accommodation reflex confirmation signal through the user input unit 160 in accordance with a sound, a display, or the like output from the control unit 190. When the control unit 190 receives the slow accommodation reflex confirmation signal, the control unit 190 stops the measurement operation and sets the position of the display 130 or the lens 140 at a time point at which the slow accommodation reflex confirmation signal is received as the far point of accommodation position P4. The near point of accommodation position P3 is set in a similar manner. Accordingly, the fast accommodation range FAR including the range between the far point of accommodation position P4 and the near point of accommodation position P3 is set.

In an example, the control unit 190 may automatically set the near point of accommodation position P3 and the far point of accommodation position P4. A middle point of a statistically average accommodation range at the user's age may be set as the user reference position, or a position at which the user can see most comfortably when the display 130 or the lens 140 is moved forward or backward at a predetermined speed within the line of sight range may be set as the user reference position in accordance with the input from the user, and the control unit 190 may decide positions which are at predetermined distance from the user reference position as the near point of accommodation position P3 and the far point of accommodation position P4. The near point of accommodation position P3 and the far point of accommodation position P4 may be set based on the age of the user.

The near slow accommodation range SAR1 and the far slow accommodation range SAR2 may be decided on the basis of the first near point of accommodation position P3 and the first far point of accommodation position P4. The near slow accommodation range SAR1 includes a range between second first near point of accommodation position P5 and the first near point of accommodation position P3, and the far slow accommodation range SAR2 includes a range between the second far point of accommodation position P6 and the second far point of accommodation position P4. Each of the slow accommodation ranges SAR1 and SAR2 includes a range in which accommodation reserve power of the eye is reflected. In a case in which the vision training is performed in the slow accommodation ranges SAR1 and SAR2, it is possible to improve the vision of the user by expanding the accommodation reserve power and the accommodation power of the user.

In a case in which the near slow accommodation range SAR1 and the far slow accommodation range SAR2 are set, it is desirable for the control unit 190 to include at least a part of the near slow accommodation range SAR1 or the far slow accommodation range SAR2 in the training range. The training range may include only the fast accommodation range FAR, but it is effective in improving the vision when a part of at least one of the near slow accommodation range SAR1 and the far slow accommodation range SAR2 is included in the training range.

The training range may be set to a range between the near slow accommodation range SAR1 and the far slow accommodation range SAR2, a range between the near slow accommodation range SAR1 and the fast accommodation range FAR, or a range between the far slow accommodation range SAR2 and the fast accommodation range FAR. Of course, the near slow accommodation range (SAR1) or the far slow accommodation range (SAR2) may be used themselves or as a combination for the training range. The user can select any one of such training ranges or a combination thereof. If there is no selection from the user, the control unit 190 may arbitrarily set or select the training range.

When the training range is set, the control unit 190 performs control such that the display 130 or the lens 140 is moved within the training range. The control unit 190 can cause the display 130 or the lens 140 to be moved continuously or intermittently. The control unit 190 may control such that the display 130 or the lens 140 performs continuous reciprocating movement within the training range or repeatedly performs movement in which the display 130 or the lens 140 is moved by a predetermined distance within the set training range and then stays for a set waiting time. Such movement of the display 130 or the lens 140 along the fixation axis produces the similar effect as when the diopter value of the lens 140 or the refractive index is changed.

The image size of the target image TI may vary depending on a distance. For example, a setting may be performed so that as the display 130 or lens 140 approaches the eyepiece unit 124, the image size gradually decreases, whereas as the display 130 or lens 140 moves towards the far position P2, the image size gradually increases. Accordingly, it is possible to measure the accommodation power or the near point of accommodation position P5 and the far point of accommodation position P6 more accurately and perform effective training.

With such training, the ciliary muscle of the user contracts or relaxes and accommodates to the change in the focal length for the target image (TI) changing with the movement of the display 130 or the lens 140, so that the ciliary muscle is strengthened.

Upon completion of the vision training, the vision training device ends the training and stores training data in the memory 180. The training data includes information related to a time until one cycle of training ends, the training mode, and the training condition. The training data is stored for each user, and the stored training data is analyzed to confirm a degree of improvement of the vision according to the training. Therefore, the user can check the degree of improvement of the vision and effectively set up a future training plan and a training direction. For example, the user can comprehend whether the vision training is performed in the SAR range or the FAR range depending on the status of the personal vision of the user such as the accommodation speed or the distance visual acuity.

The vision training device can measure the near point of accommodation position P5 and the far point of accommodation position P6 corresponding to the current status of personal vision of the user and sets the training range on the basis of the near point of accommodation position P5 and the far point of accommodation position P6, and thus high vision improvement can be provided.

Figure 9:
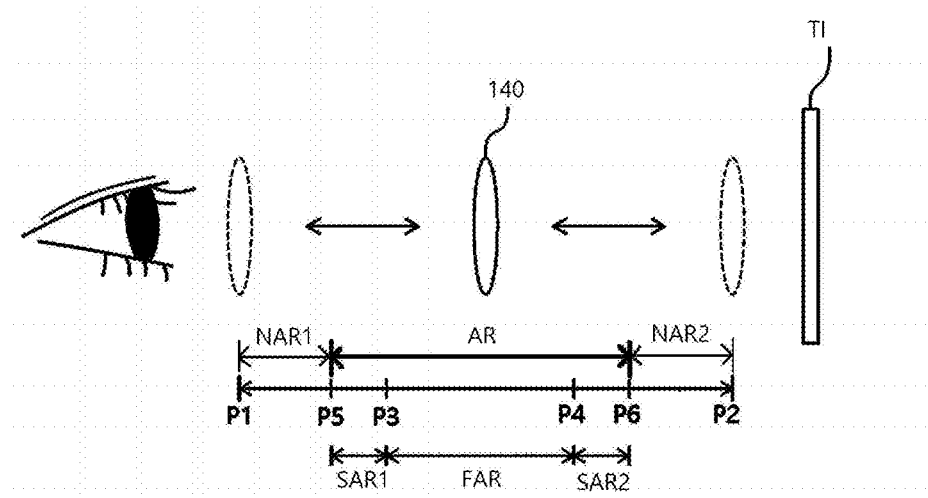
FIG. 9 is a reference diagram describing an exemplary training process based on lens movement.

FIG. 9 is a reference view for describing the training process according to the movement of the lens 140. As can be seen in FIG. 9, the vision training device changes the focal length between the target image (TI) and the eye by moving the display 130 and/or the lens 140 and thus strengthens the ciliary muscle associated with vision. The description of the measurement mode and the training mode based on the movement of the display 130 described above is similarly applied to the vision training based on the movement of the lens 140. As the lens 140 is moved, the first near point of accommodation position P3, the first far point of accommodation position P4, the second near point of accommodation position P5, and the second far point of accommodation position P6 can be measured on the basis of the position of the lens 140, the fast accommodation range FAR, the near slow accommodation range SAR1, and the far slow accommodation range SAR2 can be set on the basis of the positions, and then the vision training can be performed.

The movement of the display 130 and the movement of the lens 140 may both be performed to change the focal distance between the target image TI and the eye. In some examples, the display 130 and the lens 140 may be moved together to change the focal length between the target image TI and the eye and strengthen the ciliary muscle associated with the vision.

Figure 10:
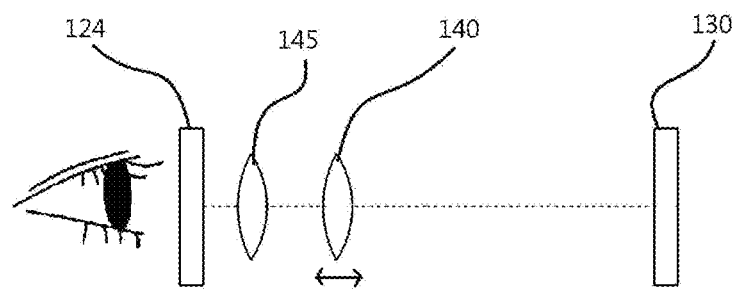
FIG. 10 is a diagram schematically illustrating an exemplary vision training device including a plurality of lenses.

FIG. 10 is an explanatory diagram schematically illustrating an exemplary vision training device. As illustrated in FIG. 10, the vision training device may include a plurality of lenses along the fixation axis. The vision training device may include a second lens 145 arranged between the eyepiece unit 124 and the lens 140 along the fixation axis. In a case in which a plurality of lenses are installed, the vision training can be performed by changing the refractive power variously rather than in a case in which a single lens is installed. The second lens 145 may be arranged between the lens 140 and the display 130. The position of the second lens 145 can be fixed or variable. The movable unit 150 may selectively move at least one of the lens 140 and the second lens 145. A piezo actuator, a voice coil motor (VCM) actuator, or an encoder actuator may be employed as the movable unit 150. The movable unit 150 may include a second movable unit for moving the second lens 145, and any of a piezo actuator, a VCM actuator, and an encoder actuator may be employed as the second movable unit 150. In addition to the second lens 145, one or more lenses that are fixed or movable and additionally affect the adjustment of the focal length may be arranged.

The image size of the target image (TI) may vary depending on the position of the display 130. For example, it is desirable that as the display 130 or the lens 140 approaches the eyepiece unit 124, the image size of the target image TI increases, and as the display 130 or the lens 140 gets away from the eyepiece unit 124, the image size of the target image TI decreases. Accordingly, accurate accommodation power measurement and the effective training can be performed.

It will be appreciated that the target image can be moved up, down, left, or right. Accordingly, it is possible to cause the muscles of the eyes to exercise in various methods.

While various embodiments in accordance with the disclosed principles have been described above, it should be understood that they have been presented by way of example only, and are not limiting.

Furthermore, the above advantages and features are provided in described embodiments, but shall not limit the application of such issued claims to processes and structures accomplishing any or all of the above advantages.

Although the invention(s) is/are described herein with reference to specific embodiments, various modifications and changes can be made without departing from the scope of the disclosure. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A vision training device, comprising:
a housing having an eyepiece unit configured to be viewed by an eye of a user;
a display configured to display a target image in front of a fixation axis of the user;
a lens disposed between the eyepiece unit and the display;
an actuator configured to move at least one of the display or the lens along the fixation axis; and
a control unit configured to: (1) set a training range within a movable range of the display and the lens, (2) control the actuator such that at least one of the display or the lens is moved within the training range, (3) set an accommodation range corresponding to a range between a near point of accommodation position and a far point of accommodation position and within the movable range, (4) determine an accommodation speed within the accommodation range based on data derived from at least one of a user input unit or a sensor, and (5) determine a training speed in the training range based on the determined accommodation speed;

wherein: (1) the accommodation speed is based on an accommodation time; and (2) the accommodation time is based on a time from when the display or lens is moved to a measurement point and a time when the user's eye transitions from a non-accommodated state to an accommodated state.

2. The vision training device according to claim 1, further comprising the user input unit, wherein the control unit is configured to set the near point of accommodation position and the far point of accommodation position in response to signals from the user input unit.

3. The vision training device according to claim 1, further comprising the sensor configured to: (a) determine if the eye of the user transitions from the accommodated state to the non-accommodated state or transitions from the non-accommodated state to the accommodated state, and (b) generate accommodation state change confirmation signals, wherein the control unit is configured to set the near point of accommodation position and the far point of accommodation position based on the accommodation state change confirmation signals.

4. The vision training device according to claim 1, wherein the control unit is configured to:

determine the near point of accommodation position and the far point of accommodation position based on the data derived from the user input unit or the sensor, and differentiate a beginning and an end of a fast accommodation range from the accommodation range based on the data derived from the user input unit or the sensor;

wherein both the beginning and the end of the fast accommodation range are between the near point of accommodation position and the far point of accommodation position.

5. The vision training device according to claim 4, wherein the control unit is configured to set the training range based on the differentiated beginning and end of the fast accommodation range.

6. The vision training device according to claim 1, further comprising a second lens disposed between the lens and the display along the fixation axis or between the lens and the eyepiece unit.

7. The vision training device according to claim 6, wherein the actuator is configured to move at least one of the lens or the second lens.

8. The vision training device according to claim 6, further comprising a second actuator configured to move the second lens along the fixation axis.

9. The vision training device according to claim 1, wherein the actuator includes one or more of a piezo actuator, a voice coil motor (VCM) actuator, or an encoder actuator.

10. The vision training device according to claim 1, wherein the display is configured such that an image size of the target image varies depending on a position of the display.

11. A vision improvement method, comprising:

providing a housing having an eyepiece unit configured to be viewed by an eye of a user, a display configured to display a target image in front of a fixation axis of the user, a lens disposed between the eyepiece unit and the display, and an actuator configured to move at least one of the display or the lens along the fixation axis;

determining a training range within a movable range of the display and the lens; and determining a near point of accommodation position and a far point of accommodation position;

determining an accommodation range corresponding to a range between the near point of accommodation position and the far point of accommodation position and within the movable range;

distinguishing between a fast accommodation range within the accommodation range and a slow accommodation range within the accommodation range;

determining an accommodation speed within the accommodation range based on data derived from at least one of a user input unit or a sensor;

determining a training speed in the training range based on the determined accommodation speed; and moving at least one of the display or the lens within the training range.

12. The vision improvement method according to claim 11, further comprising determining the near point of accommodation position and the far point of accommodation position in response to signals from the user input unit.

13. The vision improvement method according to claim 11, wherein:

the sensor is configured to: (a) determine if the eye of the user transitions from an accommodated state to a non-accommodated state or transitions from the non-accommodated state to the accommodated state, and (b) generate accommodation state change confirmation signals;

the method further comprises determining the near point of accommodation position and the far point of accommodation position based on the accommodation state change confirmation signals.

14. The vision improvement method according to claim 11, further comprising moving a second lens along the fixation axis, the second lens disposed between the lens and the display or between the lens and the eyepiece unit.

15. The vision improvement method according to claim 11, wherein an image size of the target image varies depending on a position of the display.

16. A vision training device, comprising:

a housing having an eyepiece unit configured to be viewed by an eye of a user;

a display configured to display a target image in front of a fixation axis of the user;

a lens disposed between the eyepiece unit and the display;

an actuator configured to move at least one of the display or the lens along the fixation axis; and a control unit configured to: (1) set a training range within a movable range of the display and the lens, (2) control the actuator such that at least one of the display or the lens is moved within the training range, (3) determine a near point of accommodation position and a far point of accommodation position based on data derived from at least one of a user input unit or a sensor; (4) set an accommodation range corresponding to a range between the near point of accommodation position and the far point of accommodation position and within the movable range, (5) determine an accommodation speed within the accommodation range based on the data derived from at least one of the user input unit or the sensor, (6) determine a training speed in the training range based on the determined accommodation speed; and (7) differentiate a beginning and an end of a fast accommodation range from the accommodation range based on the data derived from the user input unit or the sensor;

wherein both the beginning and the end of the fast accommodation range are between the near point of accommodation position and the far point of accommodation position.

17. The vision training device according to claim 16, wherein the control unit is configured to set the training range based on the differentiated beginning and end of the fast accommodation range.

18. The vision training device according to claim 17, further comprising the user input unit, wherein the control unit is configured to set the near point of accommodation position and the far point of accommodation position in response to signals from the user input unit.

19. The vision training device according to claim 17, further comprising the sensor configured to: (a) determine if the eye of the user transitions from an accommodated state to a non-accommodated state or transitions from the non-accommodated state to the accommodated state, and (b) generate accommodation state change confirmation signals, wherein the control unit is configured to set the near point of accommodation position and the far point of accommodation position based on the accommodation state change confirmation signals.

20. The vision training device according to claim 17, wherein the actuator includes one or more of a piezo actuator, a voice coil motor (VCM) actuator, or an encoder actuator.

* * * * *